United States Patent [19]

Evans et al.

[11] 3,933,973

[45] Jan. 20, 1976

[54] TREATMENT OF LEAD SULPHIDE BEARING MATERIAL

[75] Inventors: David John Ivor Evans, North Edmonton; Ian M. Masters, Edmonton, both of Canada

[73] Assignee: Sherritt Gordon Mines Limited, Toronto, Canada

[22] Filed: Oct. 16, 1973

[21] Appl. No.: 406,979

[52] U.S. Cl. .................. 423/93; 260/436; 423/98; 423/435; 423/571
[51] Int. Cl.[2] ................. C01G 21/14; C22B 13/04
[58] Field of Search ....... 423/89, 98, 435, 561, 567, 423/571, 92, 93; 75/101 R, 120; 260/436

[56] References Cited

UNITED STATES PATENTS

| 38,283 | 4/1863 | Cobley | 260/436 |
|---|---|---|---|
| 720,670 | 2/1903 | Charlier | 423/435 |
| 914,730 | 3/1909 | Kingsley | 423/92 |
| 1,706,143 | 3/1929 | Corbould | 75/120 |
| 1,916,302 | 7/1933 | Curtin | 423/98 |
| 1,965,880 | 7/1934 | Calbeck | 423/435 |
| 2,328,089 | 8/1943 | Mulligan | 423/98 |
| 2,839,390 | 6/1958 | Galloway | 75/120 |
| 2,950,964 | 8/1960 | Forward et al. | 423/92 |
| 3,440,155 | 4/1969 | Pickering | 423/98 |

FOREIGN PATENTS OR APPLICATIONS

| 12,492 | 4/1892 | United Kingdom | 260/436 |
|---|---|---|---|
| 867,819 | 5/1961 | United Kingdom | 75/120 |

OTHER PUBLICATIONS

Mackiw, U. N. Current Trends in Chemical Metallurgy, Can. J. Chem. Engr. V. 46 (1) Feb. 1968 pp. 3–15.

Primary Examiner—Herbert T. Carter
Assistant Examiner—Gary P. Straub
Attorney, Agent, or Firm—Frank I. Piper; Arne I. Fors; James T. Wilbur

[57] ABSTRACT

A method is disclosed for leaching finely divided lead sulphide bearing material to convert contained lead values to soluble lead acetate with concurrent conversion of sulphur values associated with the lead sulphide to an elemental state. The method involves forming a slurry consisting of the material dispersed in an aqueous medium containing free acetate ions and having a pH below 5.1. The slurry is reacted at a temperature of 60° to 120°C. with a free oxygen-bearing gas under a partial pressure of oxygen of 20 to 60 p.s.i. in order to convert lead sulphide to soluble lead acetate with concurrent production of insoluble elemental sulphur.

11 Claims, No Drawings

TREATMENT OF LEAD SULPHIDE BEARING MATERIAL

FIELD OF THE INVENTION

This invention relates to the treatment of lead sulphide-bearing material and more particularly to a leaching process for converting lead values in such material to a soluble form with concurrent conversion of sulphur values associated with the lead values to an elemental state.

DESCRIPTION OF THE PRIOR ART

Processes known for recovering lead from lead-bearing material involve leaching the material in a basic aqueous leach solution containing water soluble alkylene or alkanol amines. Canadian Pat. No. 616,515 issued Mar. 14, 1961 describes this method in detail. It is also known to leach such material in solutions of ammoniacal ammonium sulphate, sodium chloride or calcium chloride.

One of the essential requirements of such processes is that the lead be present as a sulphate, basic sulphate or an oxide (PbO). Thus, in order that the processes may be applied to sulphide ores, means must be provided for converting lead sulphide to one of the forms mentioned. The conversion can be effected in any number of ways such as by roasting, by aqueous oxidation under pressure in acid media in the manner described in the Canadian patent referred to above or by aqueous oxidation in an ammoniacal ammonium sulphate solution in the manner described in Canadian Pat. No. 701,449, issued Jan. 5, 1965.

There are a number of problems associated with these conversion methods. For example, if the lead sulphide is roasted, the temperature required to convert it to the forms mentioned is so high that there is a strong probability that some of the lead present will, on oxidizing, form silicates or other compounds which are not soluble in the amine leach solutions. In addition, the smoke and fume problems associated with lead sulphide roasting necessitates that the plant be located in areas remote from centres of population. Alternatively, costly smoke and fume treating equipment must be provided.

If the lead sulphide is converted by treatment in aqueous sulphuric acid under pressure and at a temperature at about 100°C. conversion takes place very rapidly. However, the reaction must be closely monitored and terminated when acid oxidation is complete. If the reaction is allowed to continue there is tendency for amine-insoluble compounds of lead and iron to form, especially if much zinc is present in the leach solution.

The conversion step required for treatment of lead sulphide-bearing material was necessitated by the fact that heretofore, there appeared to be no convenient leach solution for the simultaneous extraction and dissolution of lead values from such material. We have found however that there in fact exists a leach solution in which, under certain conditions, lead values may be so extracted and dissolved. There is no necessity first to convert the lead sulphide to lead sulphate or to the other forms mentioned and accordingly none of the problems associated with the conversion step are encountered. Furthermore, sulphur values associated with the lead convert to elemental form and may be readily separated as such from the leach solution.

The broad object of this present invention is to provide a method by which lead values in a lead sulphide ore may be extracted and dissolved directly in a leach solution with concurrent conversion of contained sulphur value to an insoluble elemental state without the necessity of first converting the lead sulphide to a lead sulphate, basic lead sulphate or a lead oxide.

A further object is to provide a process by which in a simple leaching operation lead in a lead sulphide-bearing ore is converted to a state such that it may be easily separated from sulphur values in a conventional liquid-solid separation step.

A still further and more specific object of the invention is a method by which lead values in a lead sulphide-bearing ore may be leached in an acetate-containing solution from which lead values may be recovered substantially free from impurities. Concurrently, sulphur values associated with the lead sulphide-bearing ore are converted to an insoluble elemental state and may be separated by, for example, filtering and may be readily recovered as such in a substantially pure state.

SUMMARY OF THE INVENTION

Broadly stated, the process which fulfills these objects involves dispersing finely divided lead sulphide-bearing material in an aqueous medium to form a slurry, providing in the slurry free acetate ions and adjusting the pH of the slurry to below about 5.1. The slurry is reacted at a temperature of between about 60°C. and about 120°C. with a free oxygen-bearing gas under a partial pressure of oxygen of between about 20 and about 60 p.s.i. The reaction is continued to oxidize the lead sulphide and to convert it to soluble lead acetate with concurrent production of insoluble elemental sulphur. Since the lead values are dissolved in solution and the sulphur values are in an insoluble elemental state, they may be readily separated from one another by means of a simple liquid-solid separation step.

DESCRIPTION OF THE PREFERRED EMBODIMENTS

The method of the present invention is described in detail hereinafter as it is applied to the treatment of commercial lead sulphide concentrates with varying lead and other metal contents. It is not, however, intended to limit the invention to the treatment of only such concentrates since the process of the invention may be applied to all ores containing economically recoverable amounts of lead sulphides.

OXIDATION LEACH

In the treatment of commercial concentrates, the mineral sulphides, preferably comminuted to particles predominantly of a size smaller than 325 mesh standard Tyler screen, are dispersed in an aqueous solution to form a slurry. The solution is acidic and must contain sufficient free acetate ions to combine with all lead values in the mineral sulphide to form lead acetate.

Preferably, a portion of the acetate ions required in solution is derived from acetic acid which acidifies the solution without, at the same time, contaminating it. It is however, undesirable to make use solely of acetic acid as a source of acetate ions since a high free acetic acid concentration in the slurry may interfere with the recovery of lead values from solution. For example, where the acetic acid concentration is relatively low, lead values may be easily converted to insoluble lead carbonate by means of carbon dioxide and may be precipitated from solution as such in the manner described in detail below. However, the presence of acetic acid in large concentrations in the solution seriously inhibits precipitation of lead carbonate by such method.

Preferably the acetic acid to lead molar ratio in the slurry is set about 3.0:1. Higher concentrations of acetic acid result, as indicated above, in poorer recovery of lead values using carbon dioxide. Furthermore, while the proportion of lead values which are extracted and converted to lead acetate increases where the molar ratio is over 3.0:1, the increase is so slight as usually not to justify the cost of additional capacity of autoclave required to contain the greater volume of acetic acid in the slurry. As the molar ratio of acetic acid to lead in the slurry decreases below about 3.0:1, the extraction and conversion of lead values falls off markedly.

The stoichiometric deficiency of acetate ions supplied by acetic acid over that required to combine with the lead values is preferably made up by means of ammonium acetate since it is readily available and does not introduce contaminants into solution. liter The rate of conversion and dissolution of lead values is dependent on the total acetate concentration and preferably to ensure a rapid conversion rate, a stoichiometric excess of acetate ions should be provided in solution. However, it is usually uneconomic to provide more than about 2 moles each of acetic acid and ammonium acetate per litre of solution since the increased rate of conversion and dissolution of lead values brought about by greater acetate concentrations can also and more economically be achieved by operating at higher temperatures or by increasing the acetic acid/ammonium acetate molar ratio.

The pH of the acetate-containing solution should be adjusted to about 5.1 or lower. At a higher pH, sulphur values associated with the starting lead sulphide material tend to convert to an oxidized form and not to an elemental state as is the case where the solution pH is 5.1 or lower. The formation of sulphate ions is undesirable because they tend to react with lead ions to produce lead sulphate which is distributed between the lead solution and the residue. Thus, separation of the lead values from sulphur values by means of a liquid-solid separation step becomes impossible.

Solution pH varies with the molar ratio of acetic acid to ammonium acetate and adjustment of the pH at the required level may be most easily accomplished by appropriate control of this molar ratio.

The slurry which contains dissolved acetate and finely divided lead sulphides is reacted in a reaction vessel such as an autoclave at a temperature between about 60°C. and about 120°C. preferably about 100°C. with a free oxygen-bearing gas such as air under a partial pressure of oxygen of above about 20 p.s.i. to about 60 p.s.i. preferably about 60 p.s.i. Higher temperatures can be used and will result in more rapid conversion and dissolution of lead values. However, at higher temperatures, there is a somewhat higher concentration of oxidized sulphur species in solution. In general, the increase in operating and equipment cost and the higher sulphate concentrations as a result of higher temperatures is not offset by an increase in lead conversion that may be obtained. Partial pressures of oxygen higher than 60 p.s.i. are usually not recommended since the proportion of lead in solution is diminished at the expense of formation of insoluble lead sulphate. At temperatures and pressures below the indicating ranges, the oxidation reaction does not occur at a practical rate.

The solids to solution ratio is preferably adjusted to provide a slurry containing from about 20 wt. percent to about 25 wt. percent solids. In most cases, a plup density above about 50% is undesirable because at such densities the slurry becomes difficult to agitate and to oxygenate.

Under these conditions the oxidation proceeds at a rapid rate, being essentially complete in about 2 hours.

The reaction may be represented as follows:

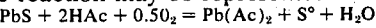
$PbS + 2HAc + 0.5O_2 = Pb(Ac)_2 + S° + H_2O$ (Ac = acetate)

At the completion of the reaction, the solution is separated from the leach residue by a conventional liquid-solid separation, such as by filtration.

TREATMENT OF LEACH RESIDUE

The separated leach residue contains in addition to elemental sulphur, lead sulphate, unreacted galena and impurities associated with the starting sulphide concentrate such as sphalerite and pyrite. Ammonium sulphide is an excellent solvent for elemental sulphur but before use may be made of it, lead sulphate, basic lead sulphate and lead oxide should be removed from the residue. Should such values not be removed, they will react with the solvent with resulting formation of lead sulphide. Since large quantities of relatively expensive ammonium sulphide solvent are consumed, the reaction is undesirable and should be prevented from taking place by removal of lead values before the solvent is combined with the residue.

The lead values may be removed from the residue using an ethylene diamine reagent according to the procedure described in Canadian Pat. No. 616,515, referred to above. The lead-containing amine solution is separated from residue by a conventional liquid-solid separation step after which elemental sulphur values may be separated from the resulting residue using the ammonium sulphide solvent.

The lead values may also be removed from the leach residue by means of ammonia. To this end, the leach residue is mixed with a dilute aqueous solution of ammonia. Preferably, the concentration of ammonia in solution or, alternatively, the solid:liquid ratio in the charge, is adjusted so that the $NH_3$ : $PbSO_4$ mole ratio in the charge is in the optimum range of 8 to 10. The resulting mixture is charged to an autoclave and maintained at a temperature of preferably about 100°C for one to 2 hours in the presence of air preferably at atmospheric pressure. Carrying out this reaction in an autoclave prevents excessive loss of ammonia from solution.

The reaction involved is the reconversion of lead sulphate or lead oxide, in the leach residues, to lead sulphide. The reaction depends upon the tendency of elemental sulphur to disproportionate into sulphide and thiosulphate ions in basic solutions as shown by the following equation:

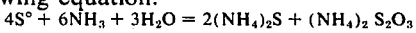
$4S° + 6NH_3 + 3H_2O = 2(NH_4)_2S + (NH_4)_2 S_2O_3$

The sulphide ion so formed acts as a so-called "sulphidizing agent" which converts $PbSO_4$ and $PbO$ to $PbS$ and sulphate ions. The overall equation for the reaction of aqueous ammonia with lead sulphate in the leach residue is believed to be as follows:

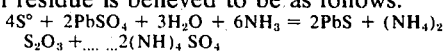
$4S° + 2PbSO_4 + 3H_2O + 6NH_3 = 2PbS + (NH_4)_2 S_2O_3 + ..... 2(NH_4) SO_4$ The residue from this reaction (PbS) is removed from solution by a conventional liquid solid separation step and may be recycled to the oxidation leach step described before for extraction and dissolution of lead values therefrom. Alternatively, the residue can be passed to a second oxidation leach stage which can be conducted under the same conditions as the aforesaid oxidation step.

The solution from the above reaction contains ammonium thiosulphate and ammonium sulphate. The solution can be oxidized to give an ammonium sulphate solution from which the ammonium sulphate can be readily recovered.

TREATMENT OF LEACH SOLUTION

The solution from the oxidation step after separation of the leach residue may be treated by one of several ways for recovery of lead values. Lead values may be recovered by electrolysis using, for example, stainless steel cathodes and anodes. Lead values migrate to both the cathode and the anode. At the anode the lead oxidizes to $PbO_2$ and at the cathode the lead stabilizes in an elemental state. The net electrowinning reaction is represented by the following equation:

$$2Pb(Ac)_2 + 2H_2O = Pb° + PbO_2 + 4HAc$$

The acetic acid (HAc) generated during electrowinning may be recirculated to the oxidation step. A subsequent reduction step must be provided to convert lead dioxide to metallic lead.

As an alternative to electrolysis, lead values may be recovered by reacting the solution with carbon dioxide. According to this procedure, the leach solution is passed to a reaction vessel such as a splash tower and carbon dioxide is fed into the solution, preferably under a pressure of about 200 p.s.i.g., to combine with dissolved lead values as insoluble lead carbonate. Preferably, the carbonation operation is conducted at room temperature. At higher temperatures, the recovery of lead is lower.

Precipitated lead carbonate can be separated from the leach solution by a conventional liquid-solid separation step such as by filtration. The separated lead carbonate solids are substantially free from the impurities with which the lead was associated in the starting lead-bearing material. This lead carbonate can be reduced to metallic lead of high purity e.g. 99.9% or higher by reacting it at a temperature of about 800°C. with a reducing agent such as natural gas in the presence of carbon in such form as graphite or petroleum coke.

Complete precipitation of lead carbonate cannot be achieved using carbon dioxide as aforesaid. It is difficult to decrease the concentration of lead in solution below 40–50 g.p.l. Following separation from the solution of the basic lead carbonate precipitate, the solution which contains lead acetate, acetic acid and ammonium acetate may be recycled to the oxidation leaching stage or may be passed to a second oxidation leaching stage. The feasibility of this method is demonstrated in Example 4.

EXAMPLE 1

Tests were carried out to determine the effect of temperature and oxygen pressure on the rate of conversion of lead sulphide to lead acetate. The starting ore concentrate analysed 72.85% Pb, 3.55% Zn, 0.002% Cu, 2.80% Fe, 16.0% S, trace insolubles and less than 0.05 ozs. Ag per ton. The concentrate was wet-ground in a ceramic ball mill to 98% minus 325 mesh standard Tyler screen. 568 gram samples of the ground material were combined with 2000 ml. samples of a solution containing 3.0 moles/l. acetic acid and 1.0 moles/l. ammonium acetate. The samples of lead containing solution were charged in turn into an autoclave.

In one set of experiments, the temperature of the resulting slurry was varied from 60° to 120°C. and another set of experiments, the oxygen pressure was varied from 20 p.s.i. to 60 p.s.i. The total proportion of lead converted from a sulphide to an acetate or an acetate/sulphate mixture was monitored over a period of time and the results are set out in the following tables.

TABLE 1(a)

| Time (hrs) | Oxygen pressure (p.s.i.g.) | EFFECT OF TEMPERATURE Lead conversion (%) when temperature maintained at following values | | | |
|---|---|---|---|---|---|
| | | 60°C. | 80°C. | 100°C. | 120°C. |
| ½ | 20 | — | 42 | 52 | 50 |
| 1 | 20 | — | 56 | 62 | 58 |
| 2 | 20 | — | 71 | 75 | 71 |
| 3 | 20 | — | 81 | 84 | 80 |
| ½ | 60 | 40 | 62 | 84 | — |
| 1 | 60 | 54 | 84 | 91 | — |
| 2 | 60 | 75 | 96 | 95 | — |
| 3 | 60 | 93 | 99 | 98 | — |

TABLE 1(b)

| Time (Hrs.) | Temperature (°C.) | EFFECT OF PRESSURE Lead conversion (%) when oxygen pressure maintained at following values | | |
|---|---|---|---|---|
| | | 20 p.s.i.g. | 40 p.s.i.g. | 60 p.s.i.g. |
| ½ | 80 | 42 | 50 | 63 |
| 1 | 80 | 58 | 67 | 82 |
| 2 | 80 | 71 | 90 | 95 |
| 3 | 80 | 81 | 95 | 99 |
| ½ | 100 | 51 | 68 | 84 |
| 1 | 100 | 62 | 82 | 91 |
| 2 | 100 | 75 | 92 | 95 |
| 3 | 100 | 84 | 98 | 98 |

The results set out in Table 1(a) show that extensive oxidation of lead values requires an oxygen overpressure of greater than 20 p.s.i.g. since 20 p.s.i.g. $O_2$ is generally insufficient for the oxidation reaction to occur at a practical rate. With an adequate oxygen overpressure, extensive oxidation of galena can occur even at temperatures as low as 60°C. provided the reaction is continued for 3 hours. The results in Table 1(b) indicate that the optimum oxygen pressure and temperature are 60 p.s.i. and 100°C. respectively.

EXAMPLE 2

284 gram samples from the same wet-ground concentrate used as the starting material of Example 1 were added to 2000 ml. samples of a leach solution containing both acetic acid and ammonium acetate. The total acetate/lead molar ratio in each mixture was 8.0. The initial pH of the sample solutions was controlled by the acetic acid/ammonium acetate molar ratio. The sample mixtures were charged in turn into an autoclave and maintained at a temperature of 100°C. for four hours under an overpressure of $O_2$ of 20 p.s.i. The results are as follows:

TABLE 2

| Leaching Solution | | | Product Solution | | | | | |
|---|---|---|---|---|---|---|---|---|
| $NH_4Ac$ | HAc | Initial | Final | HAc | Pb | $S_T$ | Pb Conversion | S Conversion |
| M | M | pH | pH | M | gpl | gpl | % | to S° |
| 1 | 3 | 4.40 | 4.50 | 1.80 | 99.6 | 0.27 | 99.5 | 72.5 |
| 2 | 2 | 5.05 | 5.25 | 1.04 | 101.8 | 1.54 | 98.0 | 74.0 |
| 3 | 1 | 5.70 | 6.00 | 0.35 | 77.5 | 2.88 | 77.0 | 49.0 |
| 4 | 0 | 7.65 | 7.5 | — | 63.8 | 11.2 | 66.3 | 2.1 |

Optimum lead dissolution and elemental sulphur formation occurs at pH 5.1 or less. The effect of increasing the solution pH by lowering the acetic acid/ammonium acetate molar ratio is striking. It is evident that in neutral ammonium acetate leach solutions there is considerable oxidation of sulphur beyond the elemental sulphur stage leading to high concentrations of sulphur species in solution. The formation of elemental sulphur is therefore drastically reduced at the higher pH's.

EXAMPLE 3

Tests were carried out to determine the effect of the acetic acid/lead suulphide molar ratio in the leach slurry on the proportion of contained lead sulphide which converted to lead acetate and dissolved in solution. The proportion of sulphur values which converted to an elemental state was also determined. Varying amounts of the same wet-ground concentrates used as the starting material in Examples 1 and 2 were combined with 2000 ml. samples of a leach solution containing 3.0 moles/l. acetic acid and 1.0 moles/l. ammonium acetate with an initial pH of 4.40. The mixtures were charged in turn into an autoclave and maintained at a temperature of 100°c. for two hours under an overpressure of oxygen of 40 p.s.i. The results are as follows:

TABLE 3

| Amount of Concentrate in Initial Leach Slurry | | HAc/PbS (HAc/Pb) Mole Ratio | Product Solution | | | | | |
|---|---|---|---|---|---|---|---|---|
| g | % Solids | | Final pH | HAc M | Pb gpl | Pb Conversion (a) % | Pb Dissolution % | S Conversion to S° % |
| 284 | 12.5 | 6.0 | 4.65 | 1.90 | 95 | 99.2 | 94.9 | 73.3 |
| 568 | 22.0 | 3.0 | 4.85 | 1.09 | 175 | 98.0 | 91.0 | 67.7 |
| 852 | 30.0 | 2.0 | 5.05 | 0.71 | 218 | 84.4 | 74.8 | 58.6 |
| 1136 | 36.0 | 1.5 | 5.05 | 0.69 | 233 | 70.4 | 62.3 | 42.9 |

(a) Pb conversion is the total of the lead sulphide converted to soluble lead acetate and insoluble lead sulphate.

The optimum acetic acid/lead sulphide molar ratio for a high lead extraction and a high concentration of lead values in solution is 3.0:1. While a slightly higher lead extraction is obtained when the HAc/PbS ratio is 6.0:1, the concentration of lead in solution is half of that at a ratio of 3.0:1. In order therefore to realize the benefit of the slightly higher lead extraction, an autoclave is required having twice the volume of an autoclave required where the HAc/PbS molar ratio is 3.0:1.

Although higher concentrations of lead values in solution can be obtained by decreasing the HAc/PbS molar ratio to below 3.0:1, the proportion of lead values which convert to a soluble form is less.

Table 3 shows that an excess of acetic acid over the stoichiometric requirements is necessary for extensive dissolution of lead.

EXAMPLE 4

The example demonstrates the feasibility of leaching the lead sulphide-bearing material with recycle solution after precipitation and removal of most of the lead values from the leach solution by means of carbon dioxide. A leach recycle solution having the following composition was prepared.

| | |
|---|---|
| Pb as $Pb(Ac)_2$ | 50 g.p.l. |
| HAc | 2.42 M |
| $NH_4Ac$ | 1.00 M |
| pH | 4.6 |

Two different amounts of the same wet-ground concentrate used as the starting material in the previous examples were combined with the recycle solution. The two mixtures were charged in turn into an autoclave and maintained at a temperature of 100°C. under an overpressure of oxygen of 40 p.s.i. Other leaching conditions and the results of leaching are set out below:

TABLE 4

| Charge | | HAc/PbS (HAc/Pb) Mole Ratio | Leach Retention Time | Product Solution Pb | Pb Dis- Solution | Pb Con- version | S Con- verted to S° |
|---|---|---|---|---|---|---|---|
| Concen- trate g | Recycle Solution ml | | hr | gpl | % | % | % |
| 385 | 2000 | 3.6 | 2.0 | 174.8 | 88.0 | 96.0 | 67.1 |
| 800 | 4000 | 3.4 | 2.5 | 178.1 | 86.9 | 98.5 | 66.9 |

The recycle solutions contain less free acetic acid than the solutions employed in Example 3. Therefore, the amounts of concentrate slurried with the recycle solution must be less than what was found to be optimum in Table 3 in order to give a HAc/PbS mole ratio of 3.0:1 or higher. A comparison of the data in Table 4 with that in Table 3 shows this to be the case. The results using recycle solution and a charge consisting of 400 g concentrate/2000 ml solution are equivalent to the results obtained using a solution with no initial lead content and a charge consisting of 568 g concentrate/2000 ml solution.

EXAMPLE 5

In this example, a number of tests were run to determine the optimum $NH_3 : PbSO_4$ mole ratio for the reaction in which lead sulphate values in the oxidation leach residue are converted to lead sulphide by means of ammonia.

Leach residues, containing about 10 to 30 wt per cent lead as lead sulphate, were mixed with ammonia solutions varying from 0.75 to 6.0 M ammonia. The resulting mixtures were charged to an autoclave and heated to 100°C. for one to 2 hours with air in the autoclave head space.

The results are shown in Table 5 following.

Table 5 shows the effect of the $NH_3/PbSO_4$ mole ratio on conversion of lead values to lead sulphide over a wide range of pulp densities and initial ammonia concentrations. At high $NH_3/PbSO_4$ molar ratios (> 10), the extent of conversion is satisfactory but the consumption of sulphur is high. At low $NH_3/PbSO_4$ molar ratios (< 8), the reaction does not proceed to completion and the proportion of lead values which convert to lead sulphide is low. The optimum molar ratio appears to be 8.5 to 10.

TABLE 5

Sulphidization of Leach Residues - Effect of $NH_3 : PbSO_4$ Mole Ratio

| Charge | | | | | Products | | | |
|---|---|---|---|---|---|---|---|---|
| Leach Residue | | | Solution Initial $NH_3$ Concentration, mole/l | $NH_3/PbSO_4$ M.R. in Slurry | Sulphidized Residue | | $PbSO_4$ Converted to PbS % | S° Con- sumed/Pb Reconverted Mole Ratio |
| g solids/l | $Pb_T$ % | Pb (as $PbSO_4$) % | | | $Pb_T$ % | Pb (as $PbSO_4$) % | | |
| 148 | 33.2 | 10.6 | 2.62 | 34.5 | 36.3 | 1.39 | 88.4 | 5.6 |
| 200 | 32.4 | 30.8 | 6.0 | 20.1 | 40.1 | 5.02 | 87.1 | 2.54 |
| 146 | 28.7 | 14.4 | 1.3 | 12.7 | 31.4 | 1.50 | 93.1 | 3.34 |
| 200 | 32.4 | 30.8 | 3.0 | 10.1 | 38.9 | 3.22 | 91.5 | 1.84 |
| 300 | 27.3 | 25.0 | 3.08 | 8.5 | 33.2 | 1.51 | 95.0 | 2.35 |
| 225 | 35.9 | 32.5 | 3.0 | 8.5 | 45.8 | 2.40 | 96.4 | 1.98 |
| 200 | 32.4 | 30.8 | 1.5 | 5.0 | 36.9 | 13.8 | 61.7 | 1.99 |
| 200 | 32.4 | 30.8 | 0.75 | 2.52 | 35.6 | 17.7 | 48.5 | 1.85 |

What we claim as new and desire to protect by Letters Patent of the United States is:

1. A method of leaching finely divided material containing predominantly lead sulphide to convert lead values to soluble lead acetate with concurrent conversion of sulphur values associated with said lead sulphide to elemental form which method comprises the steps of: dispersing said finely divided material in an aqueous medium to form a slurry; providing in said slurry free acetate ions; reacting said slurry at a temperature of between about 60°C and about 120°C with a free oxygen-bearing gas under a partial pressure of oxygen of between about 20 and about 60 p.s.i.; continuing said reaction to oxidize said lead sulphide and to convert it to soluble lead acetate with concurrent production of insoluble elemental sulphur; and separating solids from solution containing said soluble lead acetate; and adjusting the pH of said slurry during said reaction and up to said separation step to below about 5.1.

2. The method as claimed in claim 1 wherein at least a portion of the acetate ions are provided in said slurry by adding thereto acetic acid.

3. The method as claimed in claim 2 wherein the molar ratio of acetic acid to lead in said slurry is adjusted to about 3.0:1.

4. The method as claimed in claim 1 wherein acetate ions are provided in said slurry by adding thereto acetic acid and ammonium acetate.

5. The method as claimed in claim 4 wherein said slurry contains acetate ions in excess of that required to combine with all lead values but the ratio of acetate ions to lead ions does not exceed 6, said acetate ions being provided by adding to said slurry no more than about 2 moles each of acetic acid and ammonium acetate per liter of solution.

6. The method as claimed in claim 1, wherein the temperature of which said slurry is reacted is about 100°C.

7. The method as claimed in claim 1 wherein the partial pressure of oxygen over said slurry is about 60 p.s.i.

8. The method as claimed in claim 1 wherein the solids to solution weight ratio of said slurry prior to said reaction is about 1/5 to ¼.

9. A method of treating finely divided material containing predominantly lead sulphide which comprises the steps of: dispersing said material in an aqueous medium to form a slurry; providing in said slurry free acetate ions; reacting said slurry at a temperature of between about 60°C. and about 120°C. with a free oxygen-bearing gas under a partial pressure of oxygen of between about 20 and 60 p.s.i.; continuing said reaction to oxidize said lead sulphide and to convert it to soluble lead acetate with concurrent production of insoluble elemental sulphur; separating solids from solution containing soluble lead acetate; adjusting the pH of said slurry during said reaction and up to said separation step to below about 5.1; and reacting said solution with a free carbon dioxide-bearing gas to convert contained lead acetate to insoluble lead carbonate thence recovering said lead carbonate.

10. The method as claimed in claim 9 wherein said solution is reacted with said free carbon dioxide-bearing gas at ambient temperature and under a positive partial pressure of carbon dioxide of about 200 p.s.i.

11. A method of treating finely divided material containing predominantly lead sulphide which comprises the steps of: dispersing said material in an aqueous medium to formm a first slurry; providing in said first slurry free acetate ions; reacting said first slurry at a temperature of between about 60°C. and about 120°C. with a free oxygen-bearing gas under a partial pressure of oxygen of between about 20 and 60 p.s.i.; continuing said reaction to oxidize said lead sulphide and to convert it to soluble lead acetate with concurrent production of insoluble elemental sulphur; separating solids from solution containing soluble lead acetate; adjusting the pH of said first slurry during said reaction and up to said separation step to below about 5.1; forming a second slurry of said solids in an aqueous ammoniacal solution in the presence of a free oxygen-bearing gas and adjusting the molar ratio of ammonia to any lead sulphate in said second slurry to between about 8 to about 10 to convert any lead values contained in said solids to lead sulphides; thence separating undissolved residue from said second slurry and recycling said undissolved residue to said first slurry.

* * * * *